US00PP34363P2

(12) United States Plant Patent
Hansen

(10) Patent No.: US PP34,363 P2
(45) Date of Patent: Jun. 21, 2022

(54) **X *MANGAVE* PLANT NAMED 'PINEAPPLE SMOOTHIE'**

(50) Latin Name: **X *Mangave***
Varietal Denomination: Pineapple Smoothie

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 67 days.

(21) Appl. No.: 17/300,741

(22) Filed: Oct. 14, 2021

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Karen M Redden

(57) ABSTRACT

A new and distinct x *Mangave* plant named 'Pineapple Smoothie' characterized by moderate to rapid growth rate and compact habit of stiff, upright to outward pointing, succulent foliage gray-green coloring and burgundy speckling in the leaf centers and cherry red in the margins. The leaves have a creamy white margin. The new plant is suitable for use in the landscape or as a potted plant.

3 Drawing Sheets

Botanical classification: x *Mangave*.
Variety denomination: 'Pineapple Smoothie'.

STATEMENT REGARDING PRIOR DISCLOSURES UNDER 37 CFR 1.77(b)(6)

No plants of x *Mangave* 'Pineapple Smoothie' have been sold, by this name or any other name, in this country or anywhere in the world, nor has any disclosure of the new plant been made prior the filing date of this application.

BACKGROUND OF THE INVENTION

The present invention relates to the new and distinct X *Mangave* plant, X *Mangave* 'Pineapple Smoothie' discovered by the inventor at a wholesale perennial nursery in Zeeland, Mich., USA as a single, individual, whole-plant mutation in a tissue culture batch of x *Mangave* 'Pineapple Express' U.S. Plant Pat. No. 28,613. The mutation was found on Feb. 10, 2021. Through repeated trials beginning in 2021 at the same nursery the new plant was referred to by the breeder code 21-SP-MANG-1010. The new plant has been successfully asexually propagated by division at the same nursery in Zeeland, Mich. Asexually propagated divisions have been found to produce stable and identical plants that maintain all the unique characteristics of the original plant.

BRIEF SUMMARY OF THE INVENTION

X *Mangave* 'Pineapple Smoothie' differs from its parents as well as all other *Manfreda, Agave* and x *Mangave* known to the applicant. Compared to the mutation parent, x *Mangave* 'Pineapple Express', the new plant has near white margins on the foliage but is very similar in habit and size. The most similar known X *Mangave* cultivars are: 'Pineapple Punch' U.S. Plant Pat. No. 32,041 'Navajo Princess' U.S. Plant Pat. No. 31,136, 'Snow Leopard' U.S. Plant Pat. No. 31,137, 'Carnival' U.S. Plant Pat. No. 31,249, 'Bridal Falls' U.S. Plant Pat. No. 33,080 and 'Kaleidoscope' U.S. Plant Pat. No. 28,614.

'Pineapple Punch' has foliage that is nearly identical in size and shape, but the margins are more yellowish. 'Navajo Princess' has more arching habit with broader, longer, more folded foliage. 'Snow Leopard' has fewer, longer and broader leaves with a lighter and a more arching habit. 'Carnival' has reverse variegation pattern with the darker color on the margin and the center of yellowish-green to yellowish-cream, and the foliage is broader, longer and more arching foliage with more spotting of greyed-purple to cherry red. 'Bridal Falls' has much broader arching foliage with larger marginal teeth. 'Kaleidoscope' has broader, longer and more arching foliage with more spotting or greyed-purple to cherry red with yellowish margins.

The new plant, 'Pineapple Smoothie', is unique from the above and all *Agave, Manfreda* and X *Mangave* known to the inventor by the following combined traits:

1. Stiff, upwardly to outwardly pointing, succulent foliage with compact habit;
2. Gray-green leaves with large speckling of burgundy in the leaf center and cherry red on the margin;
3. Moderate to rapid growth rate with good natural pup production;
4. Foliage has medium width creamy white bands along the margins.

BRIEF DESCRIPTION OF THE DRAWINGS

The drawings of the new plant demonstrates the overall appearance of the new plant including the unique traits as a one-year old plant grown in a container in a greenhouse and later moved to a full-sun trial garden with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
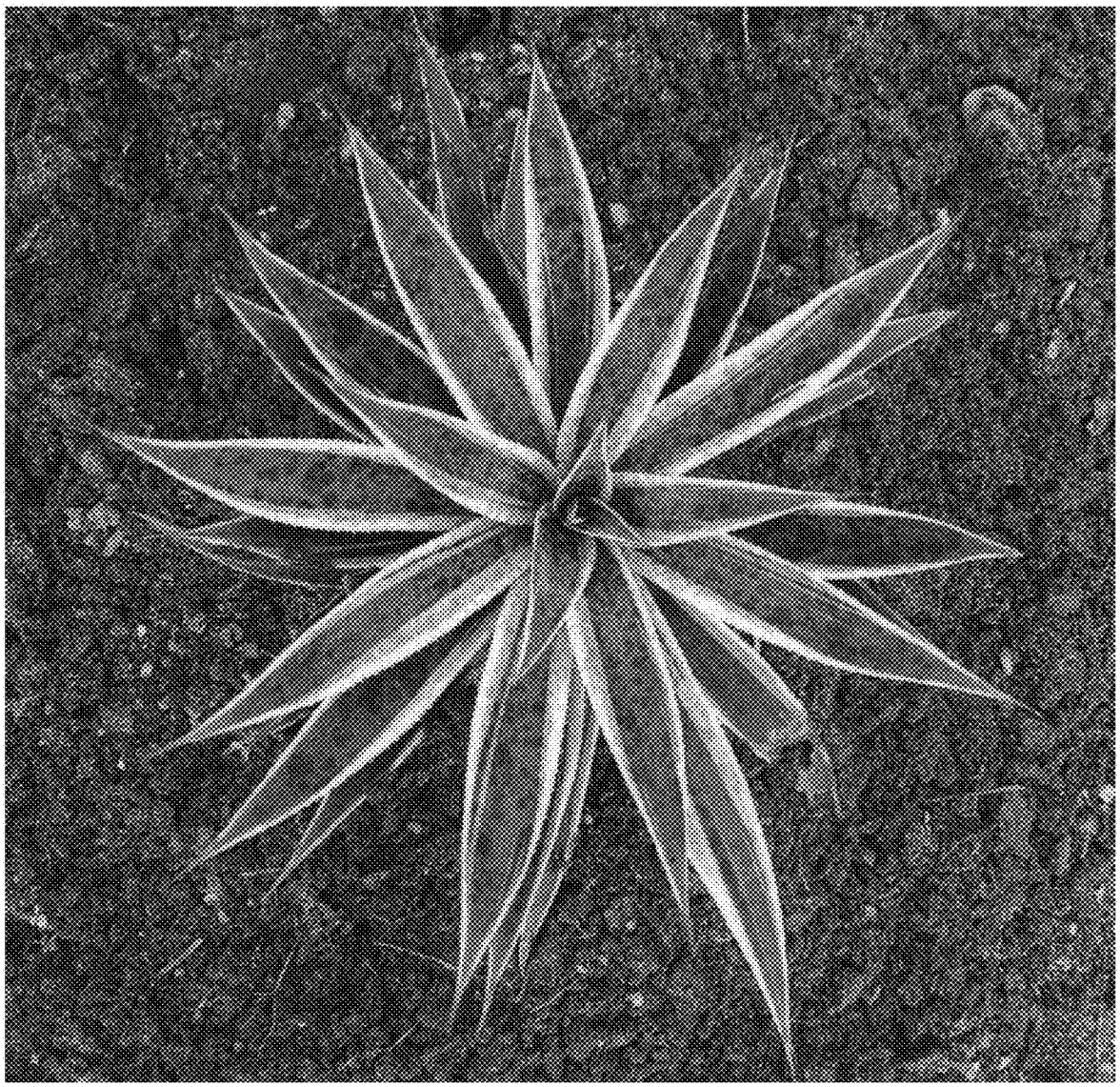
FIG. 1 shows the new plant from top view.
Figure 2:
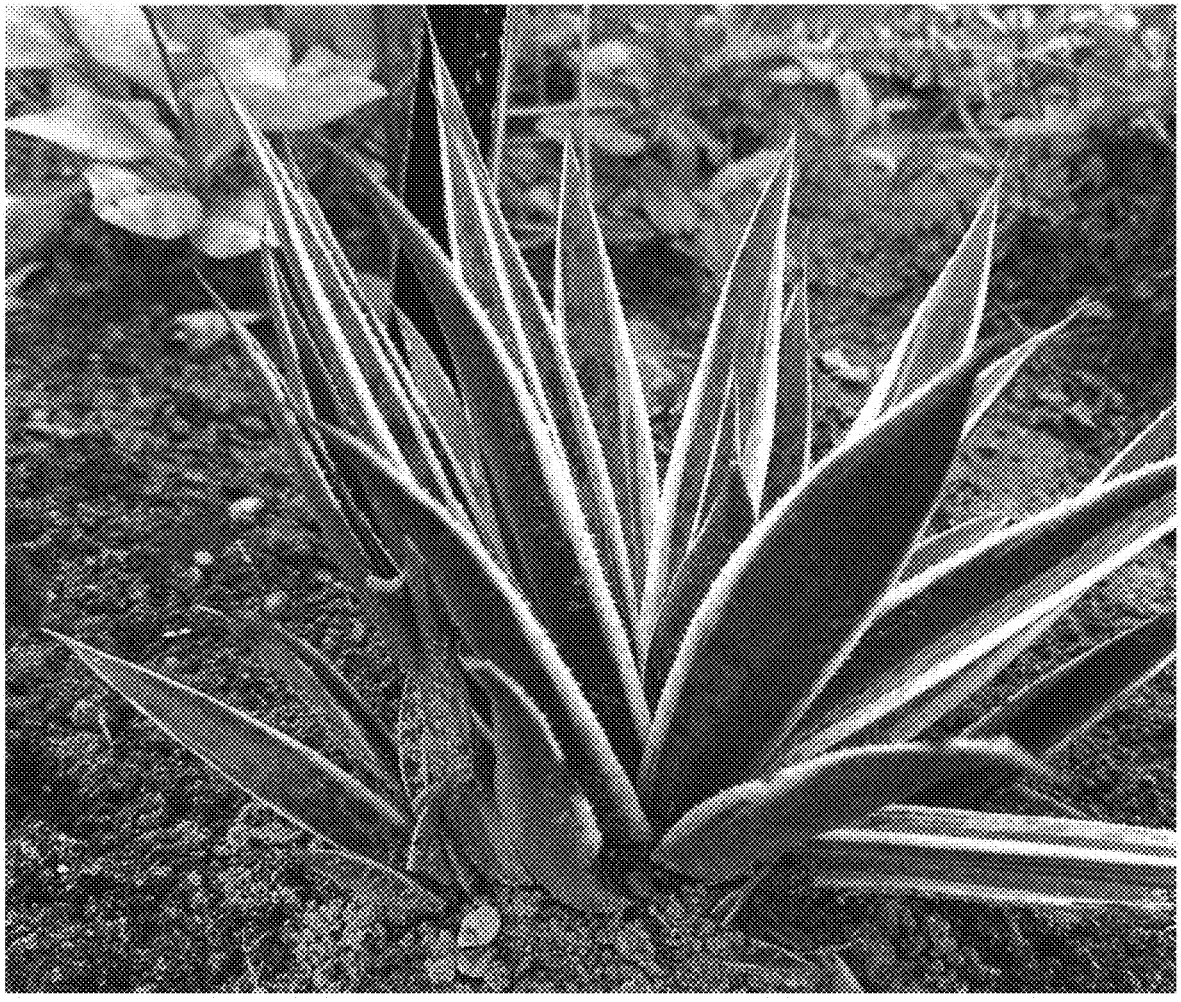
FIG. 2 shows the new plant from a side view.
Figure 3:
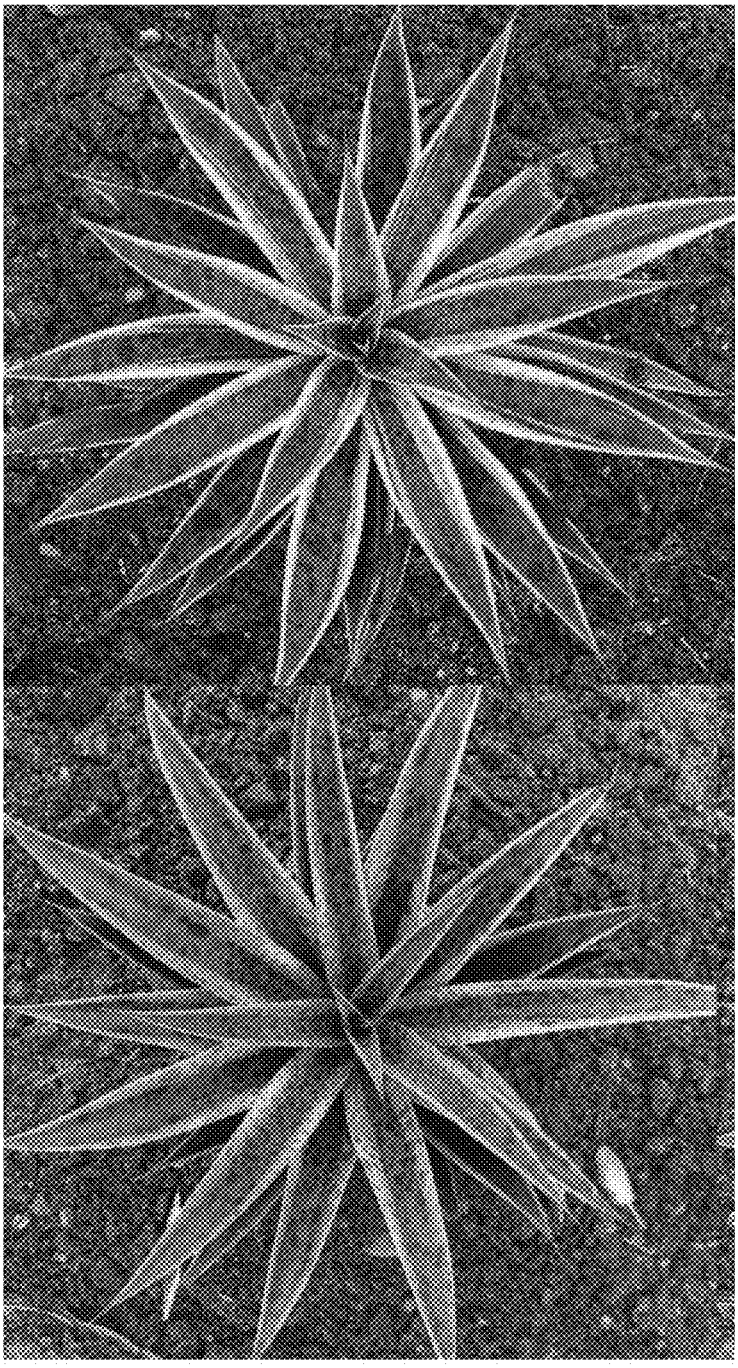
FIG. 3 shows a comparison of the new plant above with 'Pineapple Punch' below.

The following descriptions and color references are based on the 2015 edition of The Royal Horticultural Society Colour Chart except where common dictionary terms are used. The new plant, X *Mangave* 'Pineapple Smoothie', has not been observed under all possible environments. The phenotype may vary slightly with different environmental conditions, such as temperature, light, fertility, moisture and maturity levels, but without any change in the genotype. The following observations and size descriptions are of a one-year-old plant in a commercial wholesale greenhouse a later planted in a full-sun trial garden in Zeeland, Mich. with supplemental water and fertilizer as needed.

Botanical classification: X *Mangave;*

Variety denomination: 'Pineapple Smoothie';

Parentage: Mutation parent x *Mangave* 'Pineapple Express';

Propagation: Division;

Time to initiate roots from division: About 21 days; time to finish in a 3.8-liter container from division: about 4 months;

Growth rate: Moderate to rapid;

Rooting habit: Fleshy, lightly branching, with roots up to 20 cm long;

Root color: Nearest RHS 158C depending on soil type;

Plant shape and habit: Succulent, herbaceous, polycarpic perennial with basal rosettes of about 30 fleshy leaves radially emerging from central rhizome producing a symmetrical rounded mound;

Plant size: Foliage height about 15.0 cm tall from soil line to the top of the leaves and about 25.0 cm wide at the widest point at soil line; stem short, about 6 cm diameter covered with leaves;

Foliage description: Gladiate; simple, sarcous, glabrous; glaucous; margins finely dentate with flexible teeth; apex acute with mucro; base truncate, sessile, clasping; typically bi-laterally symmetrical; glabrous and glaucous adaxial and abaxial;

Number of leaves: About 30 per plant;

Leaf blade size: To about 14.0 cm long, about 2.2 cm wide near middle and 4.0 mm thick, average about 13.0 cm long, 2.0 cm wide and 3.5 mm thick; with irregularly shaped spots intensified with higher ultraviolet light of between about 1.0 diameter to about 6.0 mm across and about 10.0 mm long; creamy white margin to about 7.0 mm wide near middle of leaf on adaxial side and 3.0 mm wide on abaxial side; region between margin and center to about 3.0 mm wide on adaxial side and not significant on abaxial side;

Foliage fragrance: None observed;

Leaf Blade Color:

*Adaxial* (*young*).—Leaf center between RHS N138B and RHS 189B with irregular spots between RHS 187B and RHS N187B; leaf margin nearest RHS NN155B with speckles of between RHS N187C and RHS 186C;

*Abaxial* (*young*).—Leaf center nearest RHS N138C with irregular spots nearest a moderate blush of nearest RHS 187B; leaf margin nearest RHS NN155B with spots nearest a light blush of RHS 186C;

*Adaxial* (*mature*).—Center between RHS N138B and RHS 189B with irregular spots nearest RHS 187B; margin nearest RHS NN155D with variable spots nearest RHS 187B; region between margin and center between RHS 190B and RHS N138D with spots nearest RHS 187B; the margin color RHS NN155D jets in toward the center in an irregular lengths and widths;

*Abaxial* (*mature*).—Center nearest RHS 138A with spots between RHS 187A and RHS N187B; margin nearest RHS NN155B with variable spots between RHS 186C and RHS 186D;

Marginal teeth color: Nearest RHS NN155D;

Mucro: Semi-flexible; straight, about 5.0 mm long;

Mucro color: Between RHS 166A and RHS 183A;

Spine texture: Semi-flexible, glabrous, sharply-pointed;

Petiole: Sessile;

Veins: Parallel; not distinct;

Flower and fruit description: Not yet observed;

Disease resistance and growth requirements: X *Mangave* 'Pineapple Smoothie' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Mangave* plant named 'Pineapple Smoothie' as herein described and illustrated, suitable as a potted plant or for the garden.

* * * * *